United States Patent [19]

Amy et al.

[11] 4,277,368

[45] Jul. 7, 1981

[54] SULFUR DIOXIDE DETECTOR

[75] Inventors: J. A. Amy, Bloomington, Ind.; Harvard C. Huber, Arlington, Va.

[73] Assignee: The United States of America as represented by the Secretary of the Navy, Washington, D.C.

[21] Appl. No.: 129,061

[22] Filed: Mar. 10, 1980

[51] Int. Cl.³ .................. G01N 21/06; G01N 21/12; C09K 3/00

[52] U.S. Cl. .................. 252/408; 23/230 R; 23/230 L; 23/232 R

[58] Field of Search ............. 23/230 R, 232 R, 230 L; 422/56; 252/408

[56] References Cited

U.S. PATENT DOCUMENTS

| | | | |
|---|---|---|---|
| 2,487,077 | 11/1949 | Shepherd | 23/232 R |
| 2,785,959 | 3/1957 | Patterso et al. | 23/232 R |
| 2,855,280 | 10/1958 | McConnauchey | 23/232 R |
| 2,949,345 | 8/1960 | Clauss | 23/232 R |
| 2,953,441 | 9/1960 | Clauss | 23/232 R |
| 3,528,780 | 9/1970 | Radawski | 252/408 |
| 3,672,842 | 6/1972 | Florin | 252/408 |
| 3,681,027 | 8/1972 | Smith | 252/408 |
| 4,222,745 | 9/1980 | Cloyd | 252/408 |

OTHER PUBLICATIONS

Patterson, Jr., C. D., et al.; Annal. Chem., vol. 24, No. 10, pp. 1586-1590 (Oct. 1952).

Primary Examiner—Teddy S. Gron

[57] ABSTRACT

A composition is provided for detecting the presence of sulfur dioxide by changing color. One type of composition is prepared by mixing a small amount of finely ground potassium permanganate with finely powdered activated silica gel to produce a lilac colored material which will turn white in the presence of sulfur dioxide. Another type of composition is prepared by soaking silica gel in an aqueous solution of potassium permanganate to produce an amber colored material which will turn white in the presence of sulfur dioxide. Both types of detecting material can be combined with silicone rubber and molded into various shapes.

4 Claims, No Drawings

4,277,368

SULFUR DIOXIDE DETECTOR

BACKGROUND OF THE INVENTION

The present invention relates to an improved composition for determining the presence of sulfur dioxide.

The problems of sulfur dioxide contamination in air are well-known as sulfur dioxide can be harmful to both personnel and equipment. While exact agreement on the maximum limit of allowable concentration of sulfur dioxide for humans has not been reached, the usually accepted maximum concentration for prolonged exposure is 10 p.p.m. The presence of sulfur dioxide also can denote an equipment failure, such as a venting lithium battery.

Most currently-used methods for determining sulfur dioxide in air depend on bubbling the sample through a solution and measuring the resulting change in some chemical or physical property of the solution (or in some cases, of the gas). Both the acidic and reducing powers of sulfur dioxide are used, and many methods and modifications are in the literature. Nearly all of them require bulky non-portable apparatus or a well-equipped laboratory.

It is known to measure the concentration of sulfur dioxide in a gas mixture by aspirating a sample of the gas mixture through a solution containing a measured amount of standard iodine solution and a starch indicator until the solution is decolorized (the "Reich test"). This test is relatively simple but it gives only spot information and fails to indicate how the process is functioning between tests. Further, it requires the attention of an operator to carry out the test.

It is also known to determine and record continuously the concentration of sulfur dioxide in a gas mixture by absorbing the sulfur dioxide in a measured quantity of electrolyte of known electrical conductivity, such as an aqueous solution of hydrogen peroxide of known concentration, and measuring the change in electrical conductivity of the solution produced by absorption of the sulfur dioxide.

In U.S. Pat. No. 2,785,959, entitled "Colorimetric Determination of Sulphur Dioxide", which issued Mar. 19, 1957, to Gordon D. Patterson and Melvin G. Mellon, there is described a method of determining the concentration of sulphur dioxide in a fluid medium by means of color-changing gels. The color-changing material is produced by treating a gelable siliceous composition with a vanadate salt. The siliceous composition is preferably silica gel and the vanadate salt is preferably ammonium vanadate.

SUMMARY OF THE INVENTION

The present invention relates to a composition for determining the presence of sulfur dioxide by changing color. One type of composition is made by grinding potassium permanganate and mixing it with finely-powdered activated silica gel to produce a lilac colored material. In the presence of sulfur dioxide, the material is irreversibly bleached.

Another type of detecting material is made by soaking powdered or lump activated silica gel in aqueous potassium permanganate solution to produce an amber colored material. This material is also irreversibly bleached in the presence of sulfur dioxide.

Both types of detecting material can be used loose or mixed with a binder. One appropriate binder material is a single-component room-temperature vulcanizing silicone rubber. The rubber-indicator mixture can be cast into blocks, rings, sheets, or other shapes for use as removable detectors.

It is therefore a general object of the present invention to provide a sensitive, inexpensive chemical detector for sulfur dioxide which can be used for long-term monitoring.

Other objects, advantages and novel features of the invention will become apparent from the following detailed description of the invention.

DESCRIPTION OF THE PREFERRED EMBODIMENT

In order to have a sensitive color-change indicator, it is usually desirable to have an intensely-colored compound so that only a small amount of the compound need be used. Also, the compound should be in a finely-divided state in order to make full use of the intense color and to increase the surface-to-volume ratio and thus increase the rate of reaction. Any additional compounds, other than the colored compound, should have a high refractive index in order to scatter the colored light from the indicator compound and thus reduce the amount of the indicator compound needed for visibility.

The present invention utilizes the intensely-colored Mn (VII) and Mn (IV) ions, as these are readily reduced to colorless Mn (II) by sulfur dioxide. Potassium permanganate, $KMnO_4$, contains the Mn (VII) ion and is intensely purple. By grinding $KMnO_4$ as finely as possible with various amounts of finely-powdered activated silica gel, the intensity of the color can be reduced to any desired value. In particular, a lilac color can be produced which is quite visible, yet contains little permanganate. In tests conducted at Naval Weapons Support Center, Crane, Indiana, it has been determined that the most sensitive detectors are provided when potassium permanganate is used in small quantities, for example, in the range of about 0.1 percent to about 5 percent. While compositions containing a much higher percentage of potassium permanganate will change color in the presence of sulfur dioxide, these compositions do not have good sensitivity.

In another method of preparation, powdered or lump activated silica gel is soaked in aqueous potassium permanganate solution and some of the $MnO_4$ ions are taken into the gel and reduced to Mn (IV), which has a strong brown color. By control of the concentration of the solution, enough Mn (IV) can be introduced to impart a clearly visible amber color to the gel, although the total amount present is small. The gel is then dried in air at room temperature or somewhat higher in an oven, care being taken to avoid very high temperatures which could alter the oxidation state of the manganese. Successful compositions have been made using both powdered silica gel or lumps (1–3 mm) of silica gel. The particle size of the silica gel will determine the nature of the container used to hold the detector composition. By way of example, when lump silica gel is used, a capsule having relatively large holes can be used to contain the composition. Also, relatively large mesh bags can be used as containers.

The products produced by either one of the above-listed methods can either be used loose or mixed with a binder. By way of example, when used loose, the composition can be placed in a colorless, transparent capsule which is made of a material through which sulfur dioxide will readily diffuse. Also, the composition might be placed in a glass container which has perforations through which sulfur dioxide can pass.

The products produced by either one of the above-listed methods can also be mixed with a binder so that various shaped articles can be cast, such as blocks, rings, sheets, and the like, which can be used as removable detectors. Also, by mixing with a suitable binder, the detecting material might be painted or otherwise directly applied to a surface, such as a battery case. Care must be taken in selecting a binder so that the binder material will not react with the indicator composition. One binder material which has been satisfactorily used with the above-described indicator composition is a silicone rubber adhesive sealant manufactured by General Electric, Silicone Products Department, Waterford, New York, under the designation RTV-108. This product is a translucent and colorless one-package silicone rubber adhesive sealant which air cures to a flexible, age-resistant, broad temperature rubber without added catalyst or heat. RTV-108 withstands temperatures from −75 degress F. to +300 degrees F. for extended periods and up to +500 degrees F. for shorter time periods, and will adhere, without priming, to most substrates including wood, metals, plastics and glass. In detecting compositions made at Naval Weapons Support Center, Crane, Indiana, it has been determined that the better compositions are formulated when one part of detecting material is mixed with between 2 and 4 parts of silicone rubber. Before mixing the detecting composition with the silicone rubber, it is desirable to lower the viscosity of the unvulcanized rubber by adding a solvent, such as n-hexane, in a ratio of 1 part unvulcanized rubber to about 2 parts of n-hexane. It is important that the solvent which is used be one which will not react with potassium permanganate.

The present invention is further illustrated by the following specific example. About 5.4 mg of potassium permanganate was added to about 3.15 grams of silica gel powder and the two ingredients were thoroughly mixed and ground to produce a distinctly pink-purple powder. About one-half of this detecting mixture was placed in a small watch glass and placed inside a 250 ml beaker. Sulfur dioxide was generated inside the covered beaker by adding a small amount of diluted sulfuric acid to about 10 mg of $KHSO_3$ which had been placed inside the beaker. The pink-purple powder on the watch glass was bleached in less than 5 minutes.

OPERATION

The detecting composition is bleached irreversibly by sulfur dioxide. A change from amber-beige or purple to white therefore means that sulfur dioxide has been in contact with the detecting composition at some time in the past (or is still there), but when, cannot be determined. The bleaching effect is also cumulative, so that an occasional few sulfur dioxide molecules over a long time would produce the same effect as many at once.

It appears that the product produced by soaking silica gel in aqueous potassium permanganate solution may be considerably more sensitive than the dry mixture type. For one thing, it requires less sulfur dioxide to perform the reduction to Mn (II). For another, it may be that the Mn lies chiefly at the surface of the silica gel and is easily available for reaction, while Mn (VII), present throughout $KMnO_4$ crystals, is more difficult to reach. Also, in the product produced by soaking, the Mn ion is in much more intimate contact with the silica gel, which has strong absorptive and adsorptive properties. Water, in particular, will therefore be readily available in the gel, which may also act to concentrate sulfur dioxide from the ambient air.

The detecting compositions described can be used for long periods of time without evaporation of essential reactants. The ability to mold the detector into a ring, plug, or other shape, as well as to use it as a sheet or as a paint, means that attachment of the detector is easy. For example, rings can be placed around tubing or under screws, blocks can provide vibration protection, and plugs can be used to seal holes.

Obviously many modifications and variations of the present invention are possible in the light of the above teachings. It is therefore to be understood that the invention may be practiced otherwise than as specifically described.

We claim:

1. A method of preparing a composition for use in detecting the presence of sulfur dioxide comprising,
    first soaking activated silica gel in an aqueous solution of potassium permanganate,
    then drying said soaked silica gel,
    then dissolving silicone rubber in n-hexane,
    then mixing said dried soaked silica gel and silicone rubber solution in a ratio of about 1 part dried soaked silica gel to between about 2 and 3 parts of silicone rubber, and
    then solidifying said mixture by curing at room temperature after solvent is removed by evaporation.

2. A method of preparing a composition for detecting the presence of sulfur dioxide comprising,
    first mixing finely ground potassium permanganate and finely powdered activated silica gel,
    then dissolving silicone rubber in n-hexane,
    then mixing said mixture of potassium permanganate and activated silica gel in the silicone rubber solution, and
    then solidifying said mixture by curing at room temperature after said solvent is removed by evaporation.

3. A method of preparing a composition for use in detecting the presence of sulfur dioxide as set forth in claim 2 wherein the ratio, by weight, of activated silica gel to potassium permanganate is between about 20 to 1 to about 500 to 1.

4. A method of preparing a composition for use in detecting the presence of sulfur dioxide as set forth in claim 3 wherein the ratio, by weight, of said potassium permanganate and activated silica gel to said silicone rubber is about 1 part of indicating material to between about 2 and 3 parts of silicone rubber.

* * * * *